United States Patent [19]
Tung

[11] Patent Number: 5,562,895
[45] Date of Patent: Oct. 8, 1996

[54] METHODS AND COMPOSITIONS FOR MINERALIZING AND FLOURIDATING CALCIFIED TISSUES

[75] Inventor: Ming S. Tung, Gaithersburg, Md.

[73] Assignee: American Dental Association Health Foundation, Gaithersburg, Md.

[21] Appl. No.: 462,968

[22] Filed: Jun. 5, 1995

Related U.S. Application Data

[63] Continuation of Ser. No. 936,068, Aug. 26, 1992, Pat. No. 5,460,803.

[51] Int. Cl.$^6$ .............................. A61K 7/16; C09K 3/00; A01N 25/02; A61C 5/00
[52] U.S. Cl. .................. 424/57; 424/43; 424/44; 424/49; 424/602; 106/35; 433/215; 433/226; 433/228.1; 433/229
[58] Field of Search ................... 424/57, 43, 44, 424/49, 602; 106/35; 433/215, 226, 228.1, 229

[56] References Cited

U.S. PATENT DOCUMENTS

| | | | |
|---|---|---|---|
| 4,219,333 | 8/1980 | Harris | 8/137 |
| 5,037,639 | 8/1991 | Tung | 424/57 |
| 5,268,167 | 12/1993 | Tung | 424/52 |
| 5,427,768 | 6/1995 | Tung | 424/52 |
| 5,437,857 | 8/1995 | Tung | 424/52 |
| 5,460,803 | 10/1995 | Tung | 424/57 |

*Primary Examiner*—John Kight
*Assistant Examiner*—Louise N. Leary
*Attorney, Agent, or Firm*—Banner & Allegretti, Ltd.

[57] ABSTRACT

The invention involves new compositions and methods of use and delivery of amorphous calcium compounds such as: amorphous calcium phosphate (ACP), amorphous calcium phoshate fluoride (ACPF), amorphous calcium carbonate phosphate (ACCP), amorphous calcium carbonate phosphate fluoride (ACCPF), and amorphous calcium fluoride (ACF) for use in remineralizing and fluoridating teeth. These amorphous compounds or solutions which form the amorphous compounds, when applied either onto or into dental tissue prevent and/or repair dental weaknesses such as dental caries, exposed roots and dentin sensitivity. The compounds have the highest solubilities, fastest formation rates and fastest conversion rates (to apatite) among all the calcium phosphates under physiological conditions. Moreover, in the presence to fluoride the amorphous compound convert rapidly to fluoride containing apatite.

21 Claims, No Drawings

METHODS AND COMPOSITIONS FOR MINERALIZING AND FLOURIDATING CALCIFIED TISSUES

The invention described herein was made in the course of research partially supported by a grant from the National Institute of Dental Research.

This is a continuation of application Ser. No. 07/936,068, filed Aug. 26, 1992, now U.S. Pat. No. 5,460,803.

BACKGROUND OF THE INVENTION

1. Field of the Invention

This invention relates to certain amorphous calcium compounds that are unique in their applications as remineralizers of caries lesions, cavities and root erosions of the tooth. These amorphous compounds when further containing a fluoride compound can also be used for topical fluoridation of the teeth. When used for either fluoridation or mineralization these compounds prevent further tooth decay and actually restore the lesions caused by dental caries.

2. Description of the Prior Art

When an incipient lesion or cavity develops on the surface of a tooth, the dentist traditionally fills the cavity that forms. This procedure may prevent the decay from spreading further, but does not restore the tooth to its original state. A considerable amount of research, however, has recently been directed toward the remineralization of dental lesions. The object of this remineralization has been the deposit of hydroxyapatite, $Ca_5(PO_4)OH$, upon the surface of the tooth. Through this remineralization process further tooth decay is prevented and the tooth is restored to its original form.

In the area of remineralization of dental tissue there have been at least three approaches. One approach uses a metastable fluoride containing calcium phosphate solution supersaturated with respect to fluorapatite and hydroxyapatite which will form apatite slowly when applied. (The term apatite, as used in the present patent, includes not only pure apatite, but also apatite that includes other elements such as fluoride containing apatite.) A second method uses combinations of sparingly soluble calcium phosphates with crystallized tetracalcium phosphate and at least one different calcium phosphate in slurries or paste form. Such an approach is disclosed in U.S. Pat. No. 4,612,053 issued to Brown et al. Yet a third method uses potassium oxalate solutions to obturate the dental tubules.

These prior art methods are characterized by several practical problems. When a supersaturated solution using a single calcium phosphate is used, the remineralization process is extremely slow. The remineralization process is in fact so slow that an inconvenient amount of time is required for its completion. Another problem with the prior art methods is that as the apatite is deposited upon the teeth, the pH's of the treating solutions change. Such a change can make the solution either too acidic or too alkaline, creating the possibility of damaging the dental tissue.

Therefore, there remains a need for a treatment which achieves rapid remineralization of teeth similar to the natural process of biological mineralization, without the dissolution of the existing dental tissue.

In the area of topical fluoridation of the dental tissue there have also been at least three approaches. The first approach introduces simple fluoride containing compounds onto the surface of the dental enamel. This process relies upon the fluoride migrating through the enamel and strengthening the teeth. The second approach introduces acidulated phosphate fluoride, which involves the dissolution of some of the dental tissue and precipitation of calcium fluoride. The third approach involves an intermediate product of dicalcium phosphate dihydrate which is then converted to fluorapatite and precipitated upon the teeth. Each of these fluoridation methods is slow and inefficient and requires a long period of time in which to achieve adequate fluoridation of the dental tissue. There remains a need for a method in which fluoridation can be achieved rapidly and without damage to the teeth.

Although the prior art does not teach the use of amorphous calcium compounds for remineralization of teeth, it does refer to amorphous calcium phosphate as an aspect of the investigation of natural bone formation. See *Synthetic Amorphous Calcium Phosphate and Its Relation to Bone Mineral Structure*, Posner and Betts, ACCOUNTS OF CHEMICAL RESEARCH, Jan. 31, 1975; *An Intermediate State in Hydrolysis of Amorphous Calcium Phosphate*, Tung and Brown, CALCIFIED TISSUE INTERNATIONAL, 1983. This use, however, is significantly different from the present invention. Bone tissue is 50% organic material and 50% inorganic material, whereas dental tissue is 90% inorganic. As such, significantly different factors affect the treatment of the different tissues.

The prior art further teaches the use of amorphous tricalcium phosphate as surgical cement in teeth and bones. See U.S. Pat. No. 4,684,673 issued to Adachi. Contrary to the present invention, Adachi teaches a filler or a cement, not a composition which reconstructs the dental tissue.

SUMMARY OF THE INVENTION

The potential for application of dental remineralization is vast. Dentists fill millions of cavities each year. If these cavities were remineralized rather than filled the general dental health of the public would be increased substantially, since remineralization results in a whole tooth. The present invention seeks to provide remineralization compositions and methods that can practically be applied under a dentist's care and used in the home, and virtually replace the need for filling of the teeth.

This invention involves the use of novel remineralization materials for remineralization of teeth and novel methods for delivering these materials to the teeth and regulating their deposition in and onto the teeth. This invention particularly involves the use of amorphous calcium compounds such as: amorphous calcium phosphate (ACP), amorphous calcium phosphate fluoride (ACPF), amorphous calcium carbonate phosphate (ACCP), and amorphous calcium carbonate phosphate fluoride (ACCPF) for use in remineralizing teeth. These amorphous compounds when applied either onto or into dental tissue prevent and/or repair dental weaknesses such as dental caries, exposed roots and sensitivity. The compounds have the highest solubilities, fastest formation rates and fastest conversion rates (to apatite) among all the calcium phosphates under physiological conditions. Moreover, in the presence of fluoride the amorphous compounds convert rapidly to fluoride containing apatite.

ACCPF is of particular interest. While it has the advantageous qualities of the other amorphous calcium compounds, it is in addition the first compound which can provide four beneficial ions for the treatment of dental tissue. The inventor has for the first time, through a novel synthesis method, been able to synthesize ACCPF. Contrary to the teaching of the art the method takes advantage of the solvent qualities of ethanol. While this synthesis method has enabled the creation of ACCPF for the first time, it can also be employed to synthesize ACP, ACCP and ACPF.

In addition to the amorphous calcium compounds and the use of those compounds to treat dental tissue the present invention includes compositions and methods for delivering the amorphous calcium compounds and other beneficial substances, such as chlorhexidine, to the surface to be treated. These methods and compositions take advantage of the increased solubility of the compounds in acidic, low pH, solutions. Moreover the acidity of the solutions is controlled through the control of the conversion reaction between carbonic acid and carbon dioxide. These methods and compositions allow for the delivery of a effective quantity of treatment material to the surface to be treated.

It should be understood that while the delivery methods of the present invention were created in relation to the treatment of dental tissue, the method has applicability and advantages in other areas as well.

The advantages of the use of the amorphous compounds according to the present invention as compared to the solutions and slurries of the prior art are many. Most importantly, the use of the compounds and methods of the invention allows for the most rapid deposition of apatite upon dental tissues. Therefore, remineralization of the teeth can be achieved more quickly. In addition, the present invention provides for remineralization and refluoridation simultaneously when the amorphous calcium compound contains a fluoride.

Another significant advantage is that the present invention will not damage the teeth due to a large change in pH during the remineralization process.

Yet another advantage of the present invention is that it provides compositions and methods which can practically be used in remineralization without long term or excessive repeated treatments.

Yet a further advantage of the present invention is the provision of a composition for remineralization of teeth which can be easily formulated and easily applied to the teeth.

Thus, the present invention provides novel compositions and methods for remineralization of caries lesions that are practical. The invention also provides compositions and methods for the rapid fluoridation of teeth by the use of amorphous calcium fluoride (ACF) compounds. Moreover the invention includes methods and compositions that improve the ability to deliver beneficial substances to the dental tissue. Through the use of these compositions and these processes damaged dental tissues can be quickly and easily repaired, restoring the tooth to a whole healthy tooth.

Further objects of the inventions will become apparent with the following description of the preferred embodiments and claims.

DETAILED DESCRIPTION OF THE PREFERRED EMBODIMENTS

The inventor has found that ACP, ACPF, ACCP, ACF and ACCPF are solid solutions with variable compositions. These solutions have no long range structure; however, they are homogeneous when measured on an angstrom scale. Under physiological conditions these amorphous calcium compounds have high solubilities, high formation rates and high rates of conversion to apatite. The high rate of conversion to apatite allows the remineralization to take place at a greater speed. This speed allows for a practical method for remineralization of dental tissue without an undue number of treatments. Moreover, in the presence of fluoride, the amorphous compounds convert to fluoride-containing apatite.

The driving forces behind the precipitation of apatite from the amorphous calcium compound solutions are the temperature and the pH. The solutions can maintain higher calcium and phosphate concentrations at a lower pH and a lower temperature. Therefore as the pH or the temperature rises the solutions become supersaturated. In this supersaturated state the solutions can rapidly precipitate apatite onto a tooth.

Remineralization is accomplished by bringing the amorphous compound into contact with the dental tissue. This can be done directly, i.e., putting an amorphous compound directly on the tooth, or indirectly through a carrier, i.e., incorporating the amorphous compound in a carrier such as a gel, a chewing gum, or a toothpaste and applying the carrier to the dental tissue. Once contact is established, deposition of apatite results from the rise in pH and temperature brought on by oral conditions. Once deposited on the dental tissue the apatite will recrystallize in situ and reform the tooth.

In another embodiment of the invention, the amorphous calcium compounds are formed, in situ, as an intermediate prior to the precipitation of the apatite. Such an embodiment includes carbonated solutions containing calcium ions, fluoride ions, carbonate ions and phosphate ions, maintained under a pressurized carbon dioxide atmosphere. The solution also preferably contains a cariostatic agent, a stabilizing agent, and an adhesion enhancing agent. Under the pressurized carbon dioxide atmosphere, the solutions have a lower pH and are stable. When applied under oral conditions, carbon dioxide escapes, causing the pH to increase. This increase in pH results in a supersaturated solution and ultimately rapid precipitation of apatite. Specifically, the ACP, ACPF, ACCP, ACF or ACCPF precipitate on and into the dental tissue due to the increases in instability and precipitation rate as temperature and pH of the solution increase. The pH and degree of supersaturation (with respect to amorphous tricalcium phosphate) of one composition containing 16 mM of potassium fluoride is shown in Table 1 (below) before and after application. Before application, the composition was held under 1.5 atmosphere pressure of carbon dioxide and at 4° C.; after application, it was under normal atmosphere (0–0.01 atm) and 35° C.

TABLE 1

The pH and degree of supersaturation (with respect to amorphous tricalcium phosphate) of the solution before and after application.

| | Temp. °C. | pH | $CO_2$ Pressure (atm) | Total Carbon (mM) | Degree of Saturation |
|---|---|---|---|---|---|
| Before | 4 | 4.5 | 1.5 | 111 | under-saturation |
| After | 37 | 10.0 | 0 | 0 | $10^{5.0}$ |
| | | 7.75 | 0.005 | 5.69 | $10^{3.1}$ |
| | | 7.5 | 0.01 | 6.44 | $10^{2.6}$ |

Another feature of the invention is its capacity to fluoridate the dental tissue. When the amorphous calcium compounds exist in the presence of fluoride ions, fluoride containing apatite is precipitated. The beneficial effects of fluoride in dental tissue are well known.

As indicated above the pH is one of the factors that controls the rate of the conversion to and deposition of apatite in and onto the teeth. Therefore it is desirable to regulate the acidity of the solution and control the reaction. It has been discovered that the acidity (pH) of the solution can be regulated by controlling the conversion reaction between carbon dioxide and carbonic acid. The conversion reaction is shown below:

$$CO_2 + H_2O \longleftrightarrow H_2CO_3$$

As the above equation indicates the acidity of a system can be controlled by controlling the concentration of $CO_2$. As the concentration of $CO_2$ increases the reaction is driven to the right and the solution becomes more acidic and conversely as the $CO_2$ concentration in the atmosphere decreases the reaction will be driven to the left and the acidity will decrease.

An application where the control of the pH through the control of the $CO_2$ is especially useful is in the precipitation of materials, including apatite and chlorhexidine, from pressurized carbonated solutions or aerosols (liquid-gas systems). In such a system, the pressurized carbon dioxide drives the conversion reaction to the right and maintains the solution in an acidic state by generating carbonic acid. As the carbon dioxide is removed by exposure of the solution to the atmospheric conditions, carbonic acid will convert to carbon dioxide and the solution will become less acidic. As the solution becomes less acidic the desired material, such as apatite or chlorhexidine, is precipitated out of solution. Therefore, this system is especially appropriate for delivering compounds that have high solubility in acidic solution and precipitate out of solution in more basic conditions. Materials such as amorphous calcium compounds and synthetic saliva can be delivered to the mouth in this way and precipitated into and onto the teeth as apatite. The synthetic saliva preferably contains the same or higher concentrations of calcium ions and phosphate ions as natural saliva. The materials in one preferred embodiment would also include a complex fluoride in the pressurized carbonated solution to fluoridate the teeth. Such complex fluorides include hexafluorosilicate, monofluorophosphate and hexafluorostannnte.

The pressurized carbonated solutions of amorphous calcium compounds of the present invention have the additional advantage of being useful for treating the dentin surface of the tooth to improve the bonding of the restorative material, for example amalgams or plastics (see, Bowen patents, U.S. Pat. Nos. 4,514,527; 4,521,550; 4,588,756; 4,659,751), in conventional dental restorations. It has been found that application of the pressurized carbonated solutions to the etched dentin in preparing for restoration will improve the bond strength between the dentin and the restorative material.

It has also been found to be desirable to deliver chlorhexidine into the body and the mouth for the treatment of dental surfaces. Chlorhexidine is an antiseptic agent which has the known characteristics of aiding in the prevention of gum disease. However, delivery of chlorhexidine to the dental tissue in effective amounts has been difficult. Chlorhexidine is a base which is only slightly soluble in water under normal conditions. This solubility increases thirty times when the solution is maintained under a carbon dioxide atmosphere of 160 psi. Therefore, the pressurized carbonated solution described above is particularly effective in delivering chlorhexidine to the dental surface. It has been found that alcohol, preferably ethanol, increases the solubility of chlorhexidine. Thus, the addition of ethanol to the pressurized carbonated solution will further increase the effectiveness of the solution in delivering chlorhexidine to the dental tissue.

In addition to the amorphous calcium compounds and/or chlorhexidine discussed above, the pressurized carbonated solution may contain other beneficial substances. In particular, one embodiment of the invention includes a carbonated solution that includes a gelling compound, such as polyvinylalcohol. This gelling compound forms a gel as the acidity of the solution decreases, i.e., as the carbon dioxide escapes from the solution. The other compounds precipitating out of the solution, e.g., amorphous calcium compounds, will thus be suspended within the gel as it forms. The creation of the gel increases the contact time with the dental tissue thus increasing the efficiency of the remineralization and fluoridation process.

It should be understood that the system using pressurized carbonated solutions to control the acidity of the solution is applicable in arts other than the dental arts. For example, the system would be advantageous for the delivery of monomers which are stable in acidic solutions but polymerize in a basic solution.

A further use of the control of acidity of a reaction system through the control of the carbon dioxide - carbonic acid conversion reaction is illustrated in the following reaction:

$$3CaCO_3 + 2H_3PO_4 \rightarrow Ca_3(PO_4)_2 + 3H_2CO_3 \rightarrow 3H_2O + 3CO_2$$

The above reaction illustrates how controlling the acidity of a reaction system through control of the carbon dioxide concentration can aid in generating a desired precipitant from acidic solutions. In the above reaction a carbonate salt and an acid (or acidic salt) are dissolved in solution and make the solution acidic initially. As the carbonic acid forms, it escapes from solution as carbon dioxide. As acidity decreases the desired material, $Ca_3(PO_4)_2$, is precipitated out of solution.

The principles of this reaction are especially applicable in carriers such as a gel, a chewing gum or a toothpaste. The carbonate salt and the acid (or acidic salt) can be suspended within the gel, the toothpaste or the chewing gum to create a nonaqueous dispersion. Upon contact with an aqueous solution, such as saliva within the mouth, the reaction between the carbonate and the acid is initiated resulting in deposition of the desired material. The desired material could be either amorphous calcium compounds or more conventional remineralization materials.

This invention thus provides the compositions that contain ACP, ACPF, ACCP, ACF and ACCPF and methods that deposit the ACP, ACPF, ACCP, ACF or ACCPF on and into the tooth. The compositions are ACP, ACPF, ACCP, ACF or ACCPF themselves or solutions containing calcium, fluoride, carbonate and/or phosphate that will form ACP, ACPF, ACCP, or ACCPF when applied. Upon application, ACP, ACPF, ACCP, ACF or ACCPF remineralize and/or fluoridate the tooth and, in the case of exposed root and dentin sensitivity, obstruct the dentinal tubules. Thus use of the compositions in accord with this invention provides relief to damaged dental tissue.

Of particular interest is the composition ACCPF. As discussed above calcium, phosphate and fluoride ions all aid the remineralization of teeth. In addition bicarbonate ions also have a beneficial effect on and around the dental tissues. ACCPF is unique as applied to the remineralization of teeth. ACCPF is the first compound that can readily dissolve in the environment of teeth and provide a single source for remineralization, fluoridation, and bicarbonate. The synthesis of ACCPF has been accomplished through a novel method which is set out in detail in Example 1A below. This method employs an alcohol as solvent. The use of an alcohol is contrary to recently published reports in the literature indicating that ethanol does not favor the formation of amorphous calcium compounds. See *Rapid Precipitation of Apatite From Ethanol-Water Solutions*, E. Lerner et. al., *J. of CRYSTAL GROWTH*, Vol. 79 (1989). It has been discovered, however, that alcohols, preferably ethanol, increase the degree of supersaturation and facilitates the drying process. This new process has allowed ACCPF to be synthesized for the first time. This new process can also be used to produce ACP, ACCP, ACPF or ACF.

In the new process two solutions are created. The first solution contains calcium cations. The second solution includes the appropriate anions, which preferably include phosphate, carbonate and/or fluoride. The pH of the two solutions is preferably adjusted so as to make them basic. The two solutions are then mixed. This mixed solution further contains an alcohol, preferably ethanol. The alcohol in the mixed solution may be from the first solution, the second solution or a separate alcohol solution. The mixture of the solutions results in the precipitation of a solid. The resulting solid is then filtered out. During the filtering the solid is preferably washed with ammonium hydroxide and then with an alcohol, again, preferably ethanol. The resulting solid is then dried by an appropriate method which may include a desiccator or an oven.

The following examples serve to illustrate preparation and use of the compositions of the present invention.

EXAMPLE 1

A gel, solution, or powder containing an amorphous calcium compound (such as ACP, ACPF, or ACCP) alone or together with other beneficial ingredients such as fluoride was applied on the tooth surface. The ACP, ACPF, or ACCP was prepared in two ways: (1) ACP, ACPF or ACCP powder was first prepared by rapid mixing of high concentrations of calcium and phosphate (with or without fluoride or carbonate) at high pH (>9.0), filtration and drying; ACP, ACPF or ACCP powder was then suspended in the solution or gel; or (2) Rapid mixing of two solutions, one containing a high concentration of calcium ion such as 1.5M $Ca(NO_3)_2$, the other containing a high concentration of phosphate such as 1.5M $K_2HPO_4$ with or without fluoride or carbonate, produced ACP, ACPF or ACCP in gel form.

EXAMPLE 1A

Amorphous calcium carbonate phosphate fluoride was synthesized by: (1) adding 77.16 g. of $Ca(NO_3)_2*4H_2O$ to 559 ml. of a 0.21 molar fraction solution of ethanol; (2) adding 29.875 g. of $K_2HPO_4*3H_2O$, 18.090 g. of $K_2CO_3$, and 7.605g of KF to 1.309 l. of a 0.21 molar fraction solution of ethanol; (3) adding 31 ml. of 15.6M $NH_4OH$ to each of the above solutions; (4) mixing the two solutions together; (5) filtering the mixed solutions; (6) washing the solid with 5 l. of 50 mM $NH_4OH$ and then 2 l. of 100% ethanol during the filtering of the mixed solutions; and (7) drying the solid in a desiccator or an oven.

EXAMPLE 2

A solution or gel containing a high concentration of phosphate (such as 1.5M $K_2HPO_4$) with high pH (>9) and 1000 ppm fluoride was applied to tooth surface for 1 min., followed by application of a solution or gel containing a high concentration of calcium ions (such as 1.5M $Ca(NO_3)_2$). The combination of the two solutions result in the formation of amorphous calcium compounds. The amorphous calcium compounds then convert to fluoride containing apatite which is deposited upon the tooth.

EXAMPLE 3

A carbonated cold solution or gel (5° C. and under pressurized carbon dioxide atmosphere) is prepared containing a high concentration of calcium, $PO_4$, and F. The solution also contains cariostatic agents, strontium and tin, an adhesive enhancing agent, oxalate, and stabilizing agents such as macromolecules (polylysine or carboxy methyl cellulose) and/or hydroxyethane diphosphonate. The solution is then applied on the tooth surface. The carbon dioxide escapes from the solution under oral atmosphere and the pH of the solution increases. As ions diffuse into the tooth, they leave behind the stabilizing agents and a milieu of higher temperature. This results in an increasingly unstable solution and more rapid precipitation.

The carbonated cold solution or gel may also be prepared by mixing two cold solutions under carbon dioxide atmosphere just before the application. One solution would contains calcium and other beneficial cations and ingredients, and the other solution would contains phosphate, fluoride and other beneficial anions and ingredients.

EXAMPLE 4

Chewing gum is prepared containing ACP, ACPF or ACCP as prepared in example 1, with or without fluoride.

EXAMPLE 5

Solid powders containing mixtures of calcium salts and phosphate salts with or without fluoride or carbonate salts such as 3 mM calcium chloride, 2 mM sodium phosphate and 0.5 mM sodium fluoride, are applied directly to the tooth, used as pumice flour, or dispersed in gel, chewing gum or other nonaqueous mediums such as toothpaste which is placed in contact with the tooth. These powders are easily dissolved in saliva and then reprecipitated as ACP, ACPF or ACCP in and on the tooth.

EXAMPLE 6

A carbonated beverage or mouth rinse contains calcium ions, phosphate ions, and other ingredients which forms ACP, ACPF, or ACCP in conditions simulating the oral cavity.

EXAMPLE 7

ACCPF is prepared in accord with example 1A. The resulting solid is applied directly to the tooth surface. The ACCPF is then converted to fluoride containing apatite and bicarbonate.

EXAMPLE 8

A chewing gum is prepared incorporating ACCPF as prepared in example 1A.

EXAMPLE 9

A supersaturated aqueous solution of ACCPF, as prepared in example 1 A, is created under a pressurized carbon dioxide atmosphere. The pressurized solution is then applied to the surface of a tooth. As the carbon dioxide escapes from the solution, the solution becomes less acidic and the ACCPF precipitates out of solution onto and into the tooth.

EXAMPLE 10

A chewing gum is prepared with a calcium carbonate solid and hydrogen phosphate solid. As the gum is put into the mouth and chewed the solids dissolve in the saliva and calcium phosphate precipitates out of the resulting solution and reacts with the tooth surface for remineralization.

EXAMPLE 11

A chewing gum is prepared with a calcium carbonate solid and monocalcium dihydrogen phosphate solid. As in example 10 the gum is put into the mouth and chewed the solids dissolve in the saliva and calcium phosphate precipitates out of the resulting solution and reacts with the tooth surface for remineralization.

EXAMPLE 12

A carbon dioxide aerosol for the application of chlorhexidine to dental tissue is prepared by mixing 0.25 g. of chlorhexidine in 60 ml. of water and putting the resulting mixture under a carbon dioxide atmosphere at 160 psi. This results in an aerosol of a 8.3 mM chlorhexidine solution. (At atmospheric conditions the solubility of chlorhexidine in water is 0.28 mM). When the aerosol is applied to the dental tissue, the pressure is released and chlorhexidine is deposited onto the dental tissue.

The preferred embodiment of the present invention is now fully described. The above description, however, is only illustrative of the invention and is not intended to limit the invention in spirit or scope. Only the following claims and their equivalents limit the scope of the invention.

I claim:

1. A pressurized carbonated solution containing an acidic solution of a material more soluble in acidic solutions than in basic solutions, whereby when the pressure is released and carbon dioxide is removed, the acidity of the solution decreases and the material precipitates out of solution allowing for delivery of the material to a surface.

2. The pressurized carbonated solution of claim 1 wherein the material comprises an amorphous calcium compound and the surface comprises dental tissue.

3. The pressurized carbonated solution of claim 2 wherein the dental tissue is the dentin surface of the tooth which has been prepared to bond to a restorative material.

4. The pressurized carbonated solution of claim 2 wherein the amorphous calcium compound is amorphous calcium carbonate phosphate fluoride.

5. The pressurized carbonated solution of claim 1 wherein the material comprises chlorhexidine and the surface comprises dental tissue.

6. The pressurized carbonated solution of claim 5 further comprising ethanol.

7. The pressurized carbonated solution of claim 1 wherein the material includes a gelling agent, whereby gelling occurs as a result of the decrease in acidity of the solution.

8. The pressurized carbonated solution of claim 2 where the solution further comprises a gelling agent, whereby gelling occurs as a result of the decrease in the acidity of the solution and the amorphous calcium compound is suspended within the resulting gel.

9. The pressurized carbonated solution of claim 1 wherein the material comprises a complex fluoride, whereby when the solution is applied to dental tissue and pressure is released, carbon dioxide escapes from the solution, the acidity of the solution decreases and the complex fluoride is hydrolyzed releasing fluoride onto and into the dental tissue.

10. The pressurized carbonated solution of claim 9 wherein the complex fluoride is hexafluorosilicate.

11. The pressurized carbonated solution of claim 9 wherein the complex fluoride is monofluorophosphate.

12. The pressurized carbonated solution of claim 9 wherein the complex fluoride is hexafluorostannate.

13. The pressurized carbonated solution of claim 9 wherein the material further comprises a gelling agent, whereby gelling occurs as a result of the decrease in the acidity of the solution and the fluoride is suspended within the resulting gel.

14. A nonaqueous dispersion of a carbonate salt and an acid, or acidic salt thereof, into a nonaqueous medium, whereby when the dispersion comes in contact with an aqueous solution the carbonate salt and the acid are dissolved into the solution, earben dioxide escapes from the solution decreasing the acidity of the solution and a material of desired qualities is precipitated from the solution onto a surface.

15. The nonaqueous dispersion of claim 14 wherein the carbonate salt is calcium carbonate, the acid is hydrogen phosphate, the nonaqueous medium is selected from the group of a chewing gum, toothpaste or a gel, and the material precipitated from the solution is calcium phosphate.

16. A method for treating dental tissue with the nonaqueous dispersion of claim 15, wherein the medium is put into the mouth where saliva dissolves the calcium carbonate and the hydrogen phosphate and calcium phosphate is deposited onto and into the dental tissue.

17. The nonaqueous dispersion of claim 14 wherein the carbonate salt is calcium carbonate, the acidic salt is monocalcium dihydrogen phosphate, the nonaqueous medium is selected from the group of a chewing gum, toothpaste or a gel, and material precipitated from the solution is calcium phosphate.

18. The nonaqueous dispersion of claim 14 further comprising a dispersion of amorphous calcium fluoride into the nonaqueous medium.

19. A pressurized carbonated solution containing an acidic solution of at least one amorphous calcium compound, whereby when the pressure is released and carbon dioxide is removed, the acidity of the solution decreases and the amorphous calcium compound precipitates out of solution onto and into dental tissue.

20. The pressurized carbonated solution of claim 19 further containing chlorhexidine.

21. The pressurized carbonated solution of claim 20 further containing a gelling agent, whereby gelling occurs as a result of the decrease in acidity of the solution.

* * * * *

UNITED STATES PATENT AND TRADEMARK OFFICE
CERTIFICATE OF CORRECTION

PATENT NO.    : 5,562,895
DATED         : October 8, 1996
INVENTOR(S)   : Ming S. Tung It is certified that error appears in the above-identified patent and that said Letters Patent is hereby corrected as shown below:

Column 1,
Line 5, please replace with the following language:

-- This invention was supported in part by research grant number DE08916 to the American Dental Association Health Foundation from the National Institute of Dental Research. The Government has certain rights in this invention. --

Signed and Sealed this

Twenty-fifth Day of February, 2003

JAMES E. ROGAN
Director of the United States Patent and Trademark Office